US010856862B2

(12) United States Patent
Inoue

(10) Patent No.: US 10,856,862 B2
(45) Date of Patent: Dec. 8, 2020

(54) METHOD FOR TREATING REFLUX ESOPHAGITIS

(71) Applicant: OLYMPUS CORPORATION, Hachioji (JP)

(72) Inventor: Haruhiro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 378 days.

(21) Appl. No.: 15/925,938

(22) Filed: Mar. 20, 2018

(65) Prior Publication Data

US 2019/0290306 A1   Sep. 26, 2019

(51) Int. Cl.
*A61B 17/04* (2006.01)
*A61B 17/00* (2006.01)
*A61B 17/29* (2006.01)
*A61B 17/062* (2006.01)

(52) U.S. Cl.
CPC .......... *A61B 17/0469* (2013.01); *A61B 17/29* (2013.01); *A61B 17/00234* (2013.01); *A61B 17/0487* (2013.01); *A61B 17/062* (2013.01); *A61B 2017/00269* (2013.01); *A61B 2017/00296* (2013.01); *A61B 2017/00827* (2013.01)

(58) Field of Classification Search
CPC ...... A61B 17/0469; A61B 2017/00269; A61B 2017/00827; A61B 2017/00818
See application file for complete search history.

(56) References Cited

U.S. PATENT DOCUMENTS 7,608,093 B2 * 10/2009 Okada ................ A61B 17/0401
606/232

FOREIGN PATENT DOCUMENTS

| JP | 2002-336263 A | 11/2002 |
| JP | 2005-529710 A | 10/2005 |
| JP | 2007-267999 A | 10/2007 |
| JP | 2008-532585 A | 8/2008 |
| WO | 2004/000129 A2 | 12/2003 |
| WO | 2006/089149 A2 | 8/2006 |

* cited by examiner

*Primary Examiner* — Sarah A Simpson
(74) *Attorney, Agent, or Firm* — Oliff PLC

(57) ABSTRACT

A method for treating reflux esophagitis includes orally inserting an endoscope into a digestive canal; an esophageal side opening forming an esophageal side opening in a mucosal layer in a part of an esophagus; a tunnel forming step of introducing the endoscope between the mucosal and a muscle layer from the esophageal side opening forming a tunnel; an abdominal cavity side opening passing from the tunnel to an abdominal cavity closer to an anus; a protrusion step of a distal end portion of the endoscope passing through the tunnel from the abdominal cavity side opening into the abdominal cavity; and a stenosis forming a wrap on a part of an outer circumference of the digestive canal near the diaphragm closer to the anus using a medical instrument inserted into a channel of the endoscope in the abdominal cavity to form a local stenosis inside the digestive canal forming a wrap.

7 Claims, 16 Drawing Sheets

METHOD FOR TREATING REFLUX ESOPHAGITIS

TECHNICAL FIELD

The present invention relates to a method for treating reflux esophagitis.

BACKGROUND ART

Reflux esophagitis is disease in which the contents of the stomach including gastric acid flow back into the esophagus, stimulate the esophageal mucosa of the esophagus, and cause inflammation in the esophageal mucosa. Reflux esophagitis causes symptoms such as chronic heartburn and acid reflux.

One of the causes of the contents of the stomach including gastric acid flowing back into the esophagus is that the function of the sphincter under the esophagus (lower esophageal sphincter: LES) deteriorates. Furthermore, it is reported that gastroesophageal reflux disease is likely to occur after a per-oral endoscopic myotomy (POEM) for esophageal achalasia or after metabolic surgery.

Gastroesophageal reflux disease is treated through internal treatment, a surgical operation, or a combination thereof. However, in internal treatment, it is necessary to continuously administer internal medicine for a long period of time. Furthermore, internal treatment is not fundamental treatment and symptoms are not easily alleviated through internal treatment. On the other hand, a surgical operation such as laparoscopic Nissen surgery is fundamental treatment, but is highly invasive. Since gastroesophageal reflux disease is benign disease, it is desirable to establish less invasive oral endoscopic therapy.

Published Japanese Translation No. 2005-529710 of the PCT International Publication describes a method for treating gastroesophageal reflux disease using an endoscope. The treatment method described in Published Japanese Translation No. 2005-529710 of the PCT International Publication is a treatment method using an endoscope and has lower invasiveness than a surgical operation such as laparoscopic Nissen surgery.

SUMMARY OF THE INVENTION

A method for treating reflux esophagitis of the present invention includes: an insertion step of orally inserting an endoscope into a digestive canal; an esophageal side opening forming step of forming an esophageal side opening in a mucosal layer in a part of an esophagus; a tunnel forming step of introducing the endoscope between the mucosal layer and a muscle layer from the esophageal side opening and forming a tunnel; an abdominal cavity side opening forming step of forming an abdominal cavity side opening passing from the tunnel to an abdominal cavity at a portion closer to an anus than a diaphragm and a portion closer to the anus than the esophageal side opening; a protrusion step of protruding a distal end portion of the endoscope through the tunnel from the abdominal cavity side opening into the abdominal cavity; and a stenosis forming step of forming a wrap on at least a part of an outer circumference of the digestive canal near the diaphragm closer to the anus than the diaphragm using a medical instrument inserted into a channel of the endoscope in the abdominal cavity to form a local stenosis inside the digestive canal in which the wrap is formed.

DETAILED DESCRIPTION OF THE INVENTION

First Embodiment

Figure 1:
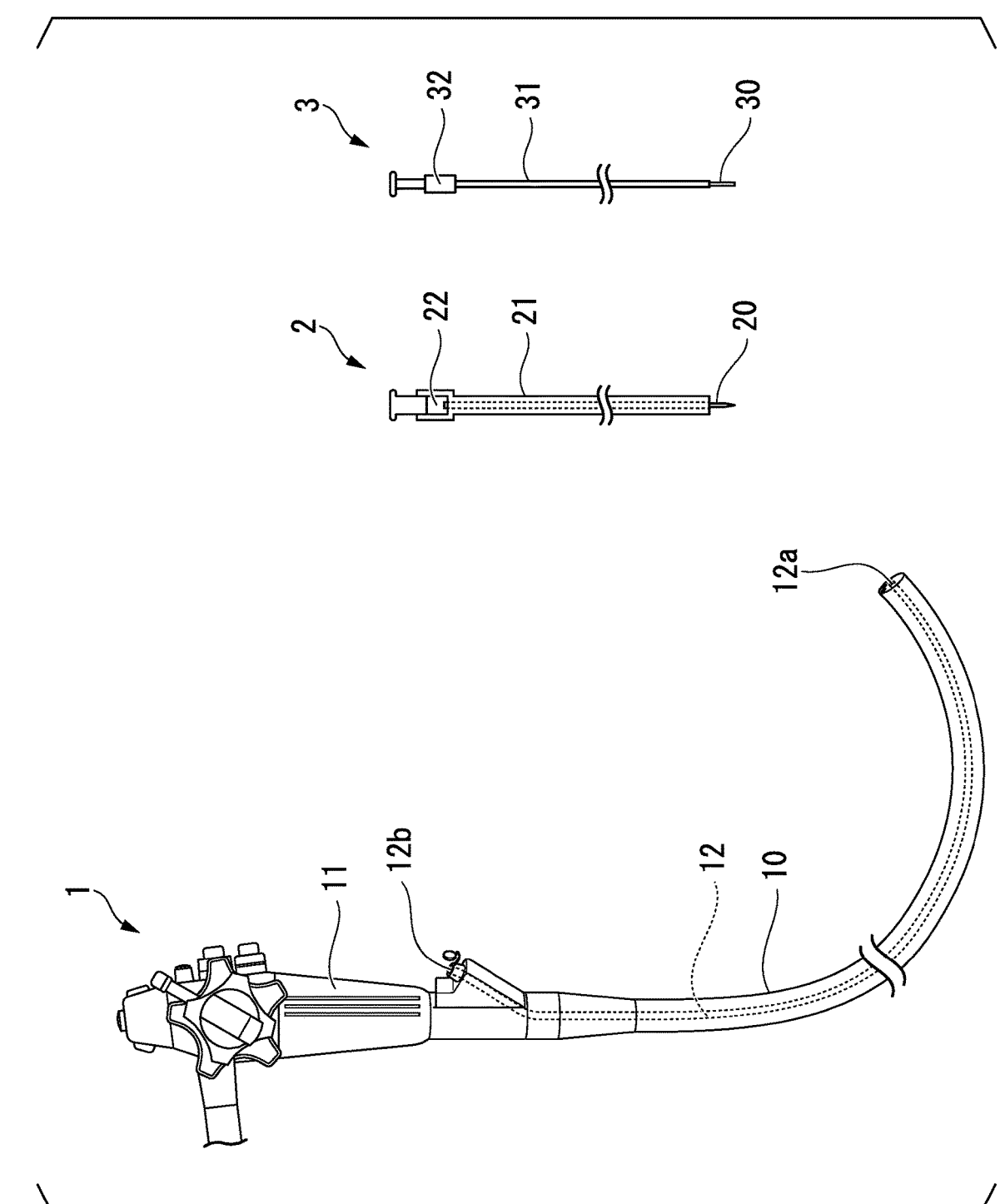
FIG. 1 is a diagram showing an overall constitution of an endoscope used in a method for treating reflux esophagitis according to a first embodiment of the present invention.

A method for treating reflux esophagitis according to a first embodiment of the present invention will be described with reference to FIGS. 1 to 12. FIG. 1 is a diagram showing an overall constitution of an endoscope 1 used in the method for treating reflux esophagitis according to the embodiment.

An operator can select and use any known endoscope which is inserted orally into a digestive canal. As illustrated in FIG. 1, the endoscope 1 used in the embodiment includes an insertion part 10 for a body cavity and a main body operation part 11 provided at a base end portion of the insertion part 10. At a distal end portion of the insertion part 10, a distal end opening portion 12a of a treatment instrument insertion channel (channel) 12 is opened. The treatment instrument insertion channel 12 is a passage extending from the distal end opening portion 12a thereof over the entire length of the insertion part 10, in which a base end portion thereof is connected to a treatment instrument introduction part 12b provided in the main body operation part 11. Treatment instruments such as a local injection means 2, a high frequency knife 3, and a grasping forceps are inserted in the treatment instrument insertion channel 12.

As illustrated in FIG. 1, the local injection means 2 is a member obtained by joining a liquid pumping part 22 such as a syringe to a base end portion of a flexible tube 21 having a needle 20 provided at its distal end and the liquid pumping part 22 is filled with physiological saline or the like as a liquid to be injected into a patient's body. The operator causes the liquid pumping part 22 to pump physiological saline or the like from the liquid pumping part 22 and allows it flow out of the needle 20 to bulge an inner wall of the body cavity.

As illustrated in FIG. 1, the high frequency knife 3 has a needle-like knife 30 at its distal end. A cable is connected to the needle-like knife 30 and the cable is inserted into a flexible cord 31. A base end portion of the flexible cord 31 is attached to a manipulator 32 and the operator can manipulate the manipulator 32 so that the needle-like knife 30 protrudes from and retracts into a distal end of the flexible cord 31. Electrodes connected to end portions of the cable are provided in the manipulator 32 and a high-frequency power source is connected to the electrodes so that a high-frequency current can flow through the needle-like knife 30.

Figure 2:
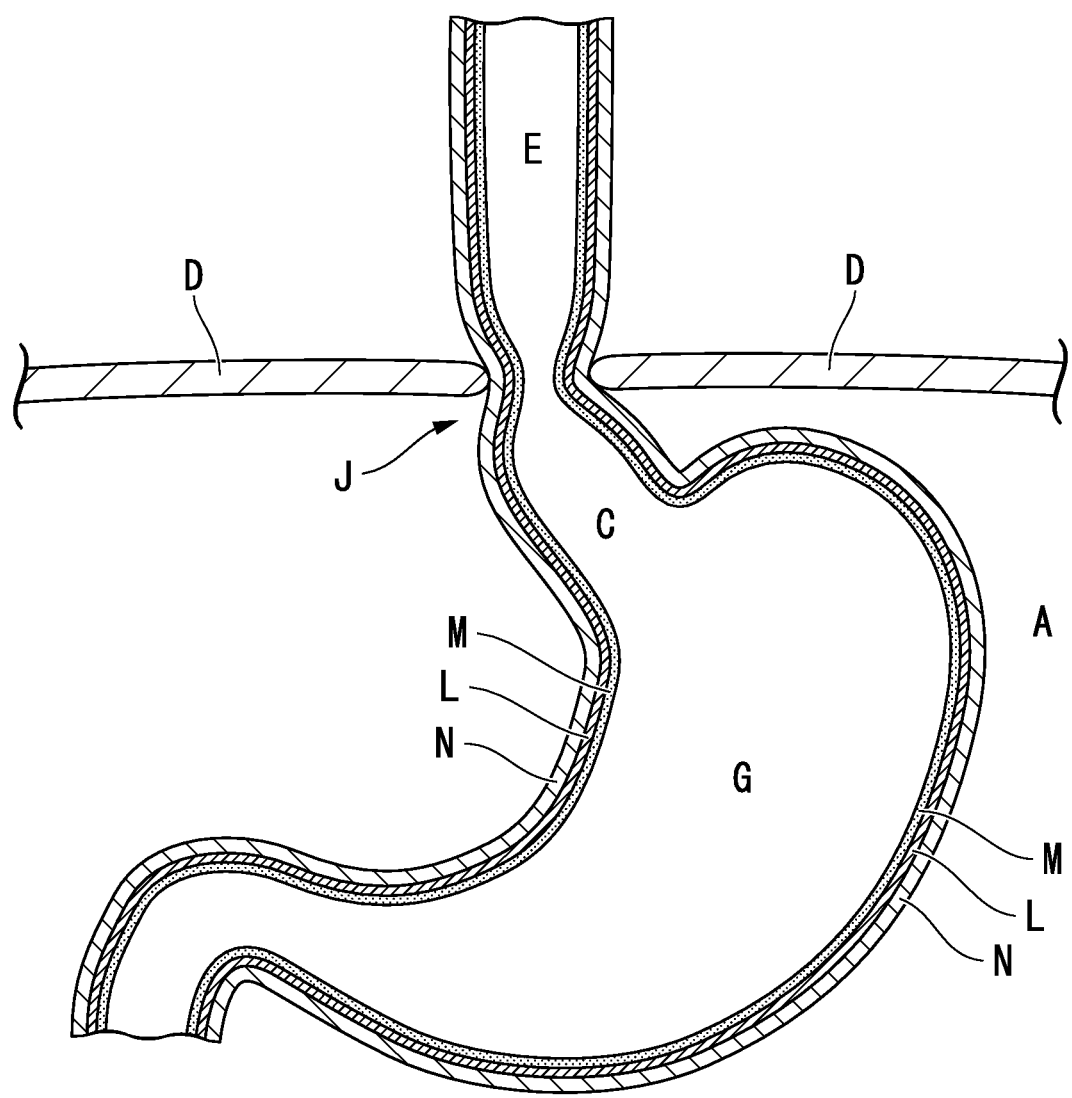
FIG. 2 is a diagram showing a digestive canal to be treated by the endoscope inserted therein in the method for treating reflux esophagitis.

Next, a site to be treated will be described with reference to the method for treating reflux esophagitis according to the embodiment. FIG. 2 is a diagram showing a digestive canal (stomach G and esophagus E) to be treated by the endoscope 1 inserted therein. A gastroesophageal junction J connected to a cardia C of the stomach G from the esophagus E of a healthy person is closed through actions of a diaphragm D or a sphincter (lower esophageal sphincter: LES) or the like, and the gastroesophageal junction J opens when food or drink enters the stomach G from the esophagus E side and the food or drink is taken into the stomach G.

Figure 3:
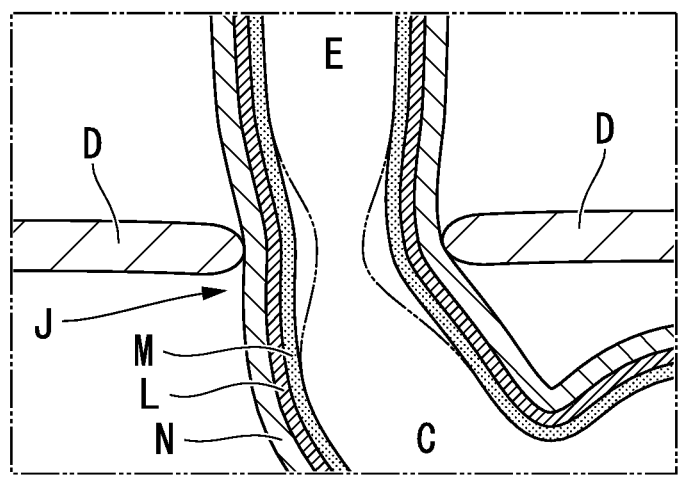
FIG. 3 is a diagram showing a gastroesophageal junction of the digestive canal of a patient with reflux esophagitis to be treated in the method for treating reflux esophagitis.

FIG. 3 is a diagram showing a gastroesophageal junction J in a digestive canal of a patient with reflux esophagitis. As illustrated in FIG. 3, the reflux esophagitis is a state in which the gastroesophageal junction J is not sufficiently closed from a normal state indicated by a broken line and thus an original anti-reflux function deteriorates. In the method for treating reflux esophagitis according to the embodiment, when a wrap is formed at at least a part of an outer circumference of the digestive canal (stomach G and esophagus E) near the diaphragm D closer to an anus than the diaphragm D, a local stenosis is formed inside the digestive canal where the wrap is formed.

Next, the method for treating reflux esophagitis according to the first embodiment will be described in detail.
[Insertion Step]
First, the operator orally inserts the endoscope 1 into the digestive canal (insertion step). The operator orally inserts the insertion part 10 of the endoscope 1 into the digestive canal and bends the distal end portion of the insertion part 10 so that the distal end opening portion 12a faces an esophagus wall.
[Esophageal Side Opening Forming Step]
Subsequently, the operator forms an esophageal side opening $O_1$ in a mucosal layer M at a part of the esophagus (esophageal side opening forming step). The operator inserts the local injection means 2 into the treatment instrument insertion channel 12 from the treatment instrument introduction part 12b. The operator protrudes the needle 20 from the distal end opening portion 12a of the treatment instrument insertion channel 12 so that the needle 20 pierces the esophagus wall. A piercing depth of the needle 20 is a length at which the needle 20 passes through the mucosal layer M but does not reach a muscle layer N and a distal end of the needle 20 is disposed in a submucosal layer L. The operator manipulates the liquid pumping part 22 to discharge physiological saline or the like from the needle 20 and bulge the esophagus wall.

Figure 4:
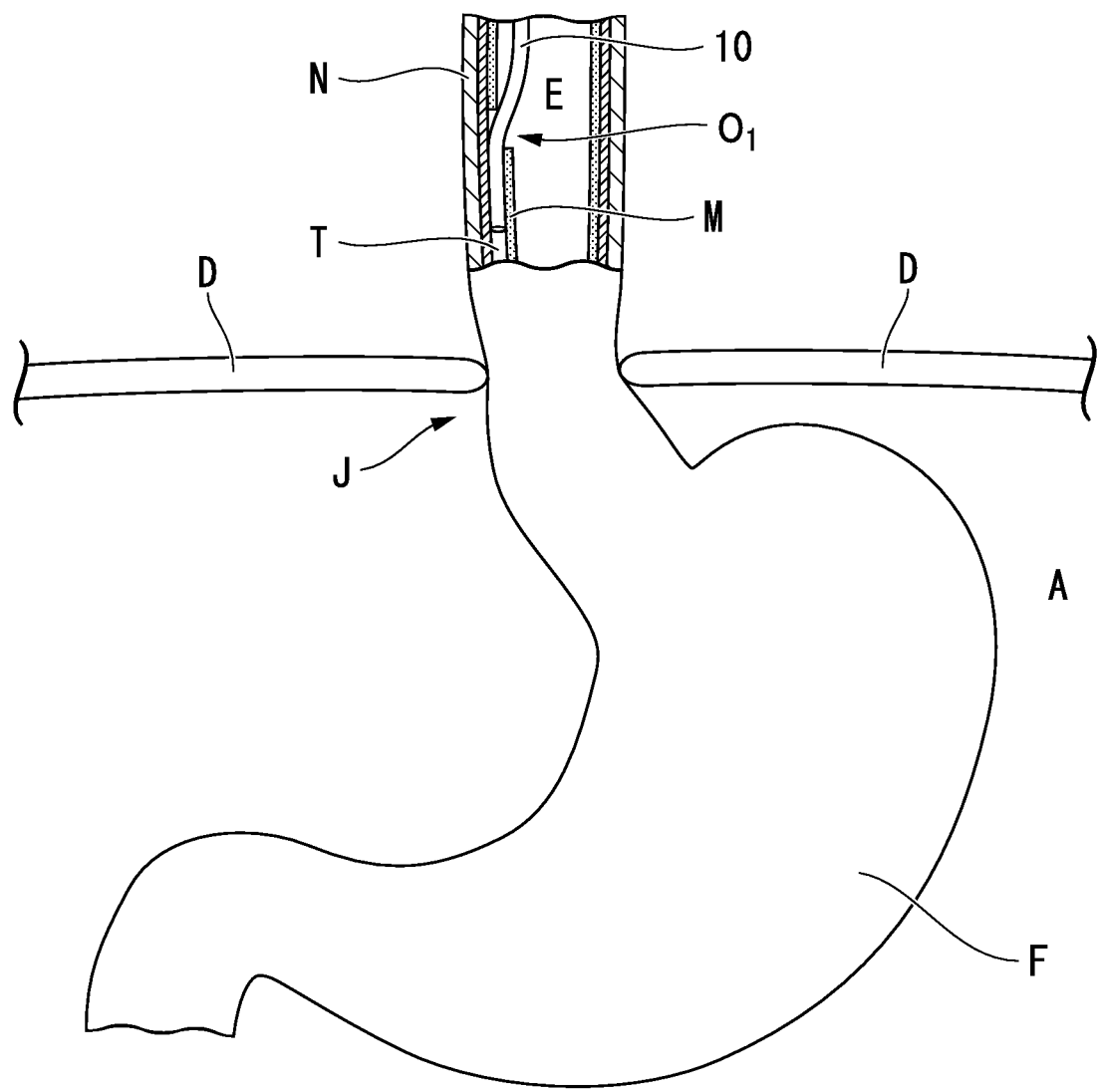
FIG. 4 is a diagram for describing a tunnel forming step in the method for treating reflux esophagitis.

The operator takes the local injection means 2 out of the treatment instrument insertion channel 12 while holding the insertion part 10 of the endoscope 1 and inserts the high frequency knife 3 into the treatment instrument insertion channel 12. Moreover, the needle-like knife 30 is caused to protrude from the distal end opening portion 12a and the bulged mucosal layer M is incised so that the esophageal side opening $O_1$ is formed in the mucosal layer M.
[Tunnel Forming Step]
FIG. 4 is a diagram for describing a tunnel forming step in the method for treating reflux esophagitis according to the embodiment. The operator introduces the endoscope 1 inward between the mucosal layer M and the muscle layer N from the esophageal side opening $O_1$ using a method that is the same as tunnel formation performed by known per-oral endoscopic myotomy (POEM) to form a tunnel T (tunnel forming step).

As illustrated in FIG. 4, the operator separates the mucosal layer M and the submucosal layer L by the high frequency knife 3 having electricity supplied thereto to form tunnels T between the mucosal layer M and the submucosal layer L, and the muscle layer N. The operator introduces the insertion part 10 inward from the esophageal side opening $O_1$ so that the tunnel T goes further inward. At this time, a hood or a cap having a shape that can easily separate the mucosal layer M may be attached to the distal end portion of the insertion part 10.

Figure 5:
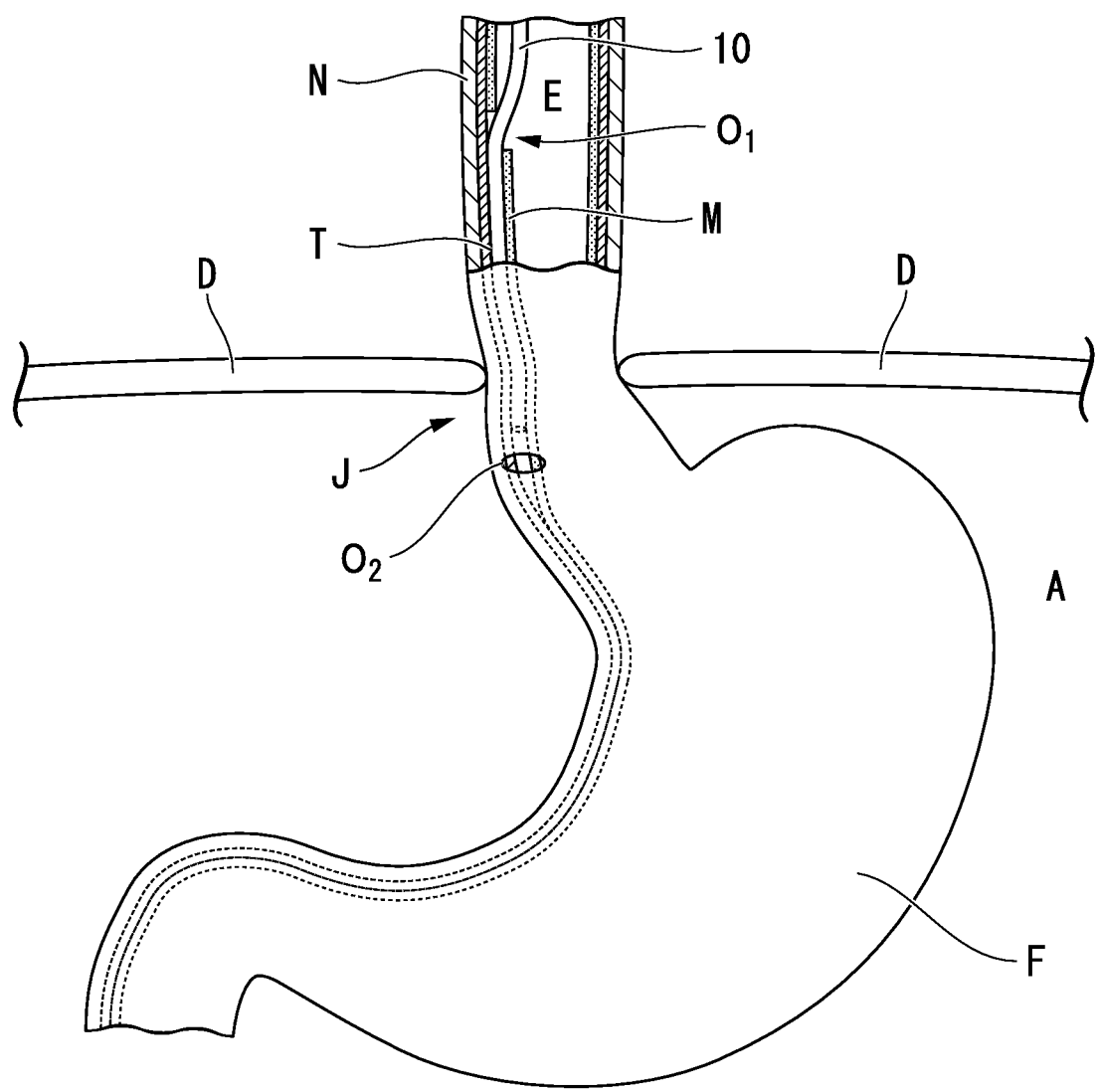
FIG. 5 is a diagram for describing an abdominal cavity side opening forming step in the method for treating reflux esophagitis.

The tunnel T is simply formed as a space generated between the mucosal layer M and the muscle layer N by pushing the submucosal layer L and this treatment does not cause any damage to the mucosal layer M or the muscle layer N.
[Abdominal Cavity Side Opening Forming Step]
FIG. 5 is a diagram for describing an abdominal cavity side opening forming step in the method for treating reflux esophagitis according to the embodiment. The operator forms an abdominal cavity side opening $O_2$ which is opened from the tunnel T to an abdominal cavity to pass through the muscle layer N and a serosa (abdominal cavity side opening forming step).

As illustrated in FIG. 5, the abdominal cavity side opening $O_2$ is closer to the anus than the esophageal side opening $O_1$ and is preferably formed in a portion thereof on the anus which is spaced 2 cm to 3 cm from the diaphragm D. The tunnel T communicates with an abdominal cavity A via the abdominal cavity side opening $O_2$.

To be specific, the abdominal cavity side opening $O_2$ is formed in the gastroesophageal junction J or a portion near the gastroesophageal junction J located closer to the anus than the diaphragm D. Thus, it is confirmed whether the abdominal cavity side opening $O_2$ is located closer to the anus than the diaphragm D before the abdominal cavity side opening $O_2$ is formed. For example, when an observation endoscope different from the endoscope 1 is inserted into the stomach and transmitted light of the endoscope 1 is observed using the observation endoscope, a position closer to the anus than the diaphragm D may be checked. Furthermore, an inside of the abdominal cavity A may be checked by a laparoscope through which observation is possible or the like. A cavity wall is stimulated by supplying electricity to the cavity wall using the high frequency knife 3 and it may be determined whether a position at which the abdominal cavity side opening $O_2$ is to be formed is located closer to the anus than the diaphragm D from a biological reaction of the diaphragm D at the time of supplying electricity.

Note that it is desirable that the abdominal cavity side opening $O_2$ be opened in a portion of the stomach G on a front wall F side thereof. This is because the abdominal cavity side opening $O_2$ opened therein on the front wall F side has a wider cavity in front of the opening as compared with a case in which the abdominal cavity side opening $O_2$ is opened therein on a rear wall side and it is easy to secure a space for performing a procedure.

The operator forms the abdominal cavity side opening $O_2$ which is opened from the tunnel T to the abdominal cavity A to pass through the muscle layer N and the serosa using the high frequency knife 3 or the like.

[Protrusion Step]

Figure 6:
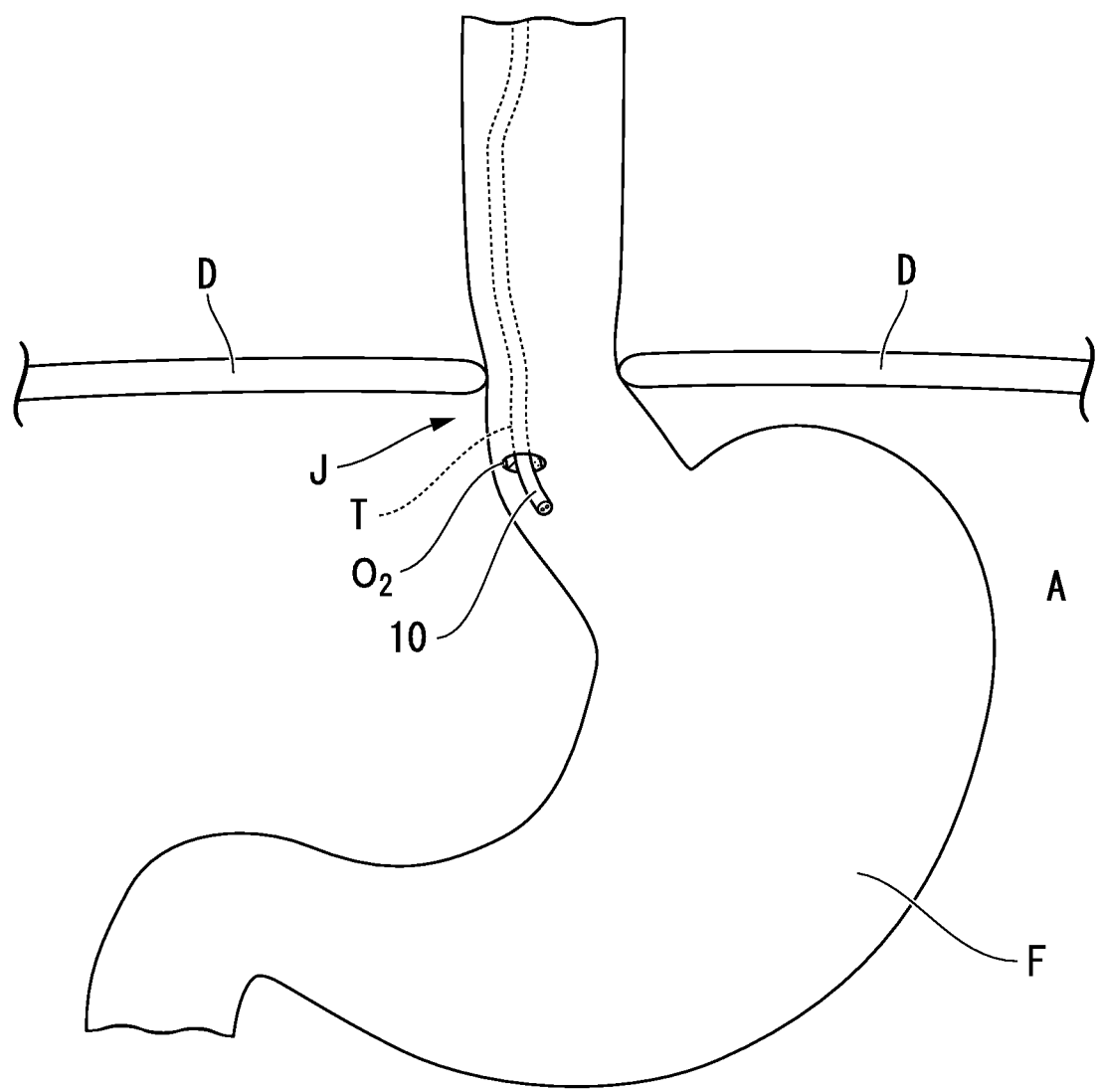
FIG. 6 is a diagram for describing a protrusion step in the method for treating reflux esophagitis.

FIG. 6 is a diagram for describing a protrusion step in the method for treating reflux esophagitis according to the embodiment. The operator causes the distal end portion of the insertion part 10 of the endoscope 1 introduced into the tunnel T to protrude into the abdominal cavity via the abdominal cavity side opening $O_2$ (protrusion step). Since the abdominal cavity side opening $O_2$ is opened in the abdominal cavity A, the operator can deliver the insertion part 10 of the endoscope 1 from the tunnel T into the abdominal cavity A via the abdominal cavity side opening $O_2$.

[Stenosis Forming Step]

FIGS. 7 to 12 are diagrams for describing a stenosis forming step in the method for treating reflux esophagitis according to the embodiment. The operator causes a local stenosis to be generated inside the digestive canal in which a wrap is formed by forming the wrap at least a part of the outer circumference of the digestive canal (stomach G and esophagus E) near the diaphragm D closer to the anus than the diaphragm D using a medical instrument inserted into the treatment instrument insertion channel 12 of the endoscope 1 inside the abdominal cavity A (stenosis forming step).

Figure 7:
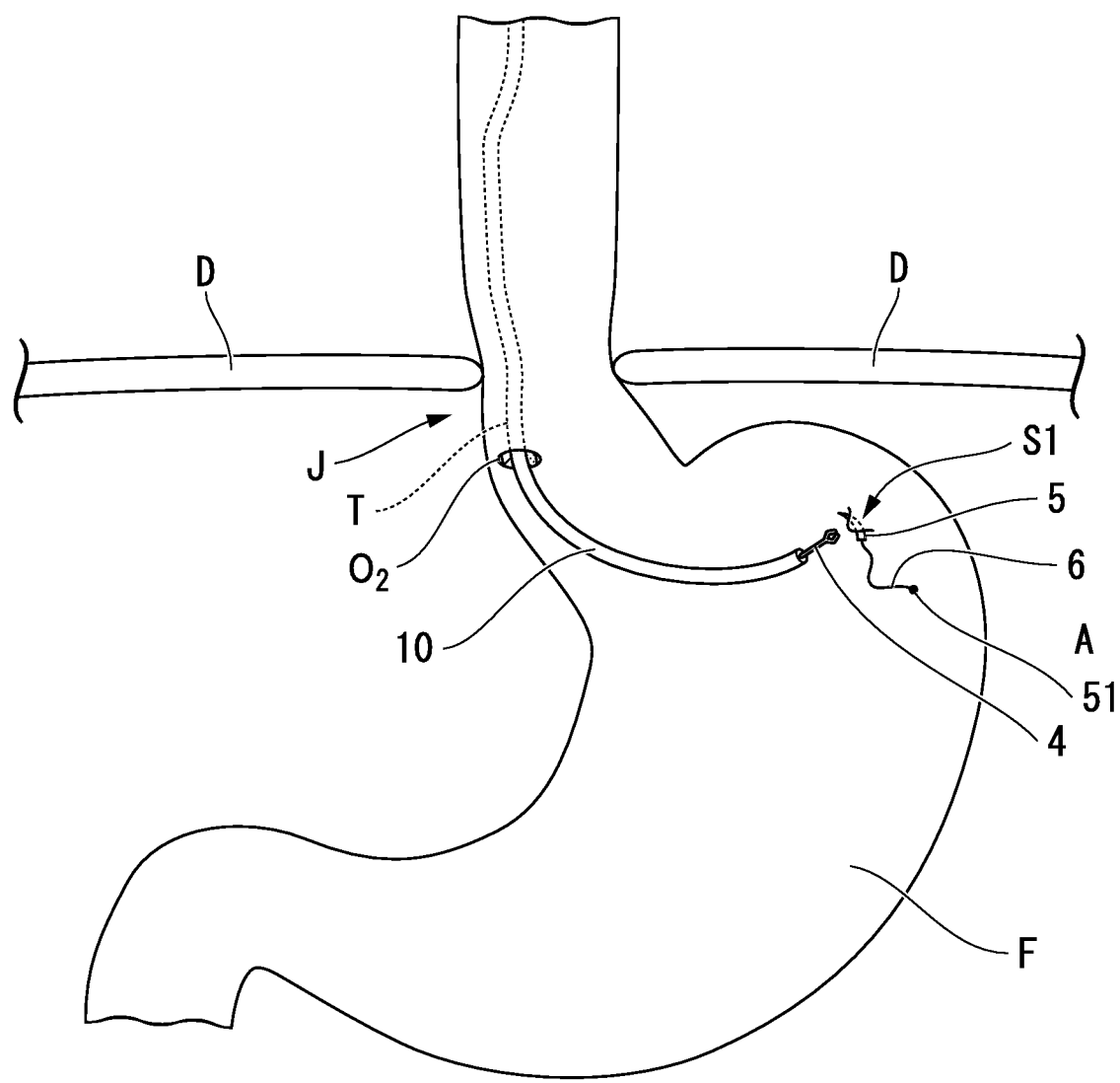
FIG. 7 is a diagram for describing a stenosis forming step in the method for treating reflux esophagitis.

The operator pulls the endoscope 1 out of the patient's body once, grips a suturing needle 5 by a needle holder 4 protruding from the distal end opening portion 12a of the insertion part 10 in the endoscope 1, and accommodates the needle in a distal end attachment if possible. In this state, the endoscope 1 is advanced into the tunnel T, the endoscope 1 is caused to protrude from the abdominal cavity side opening $O_2$ to the abdominal cavity A, and the suturing needle 5 to which a suture thread 6 is attached is delivered inside the abdominal cavity A using the needle holder 4. As illustrated in FIG. 7, the operator sutures the suture thread 6 to a part of the front wall F of the stomach G away from the abdominal cavity side opening $O_2$ (hereinafter referred to as a "first suture region (first treatment region) S1") using the suturing needle 5. The operator inserts the distal end of the suturing needle 5 into an outer surface of a canal wall (stomach wall), causes a distal end of the suturing needle 5 to pierce along the bending of the suturing needle 5 until the distal end of the suturing needle 5 is appeared from the outer surface of the canal wall (stomach wall) again, and then pulls out the appeared distal end using the needle holder 4.

Figure 8:
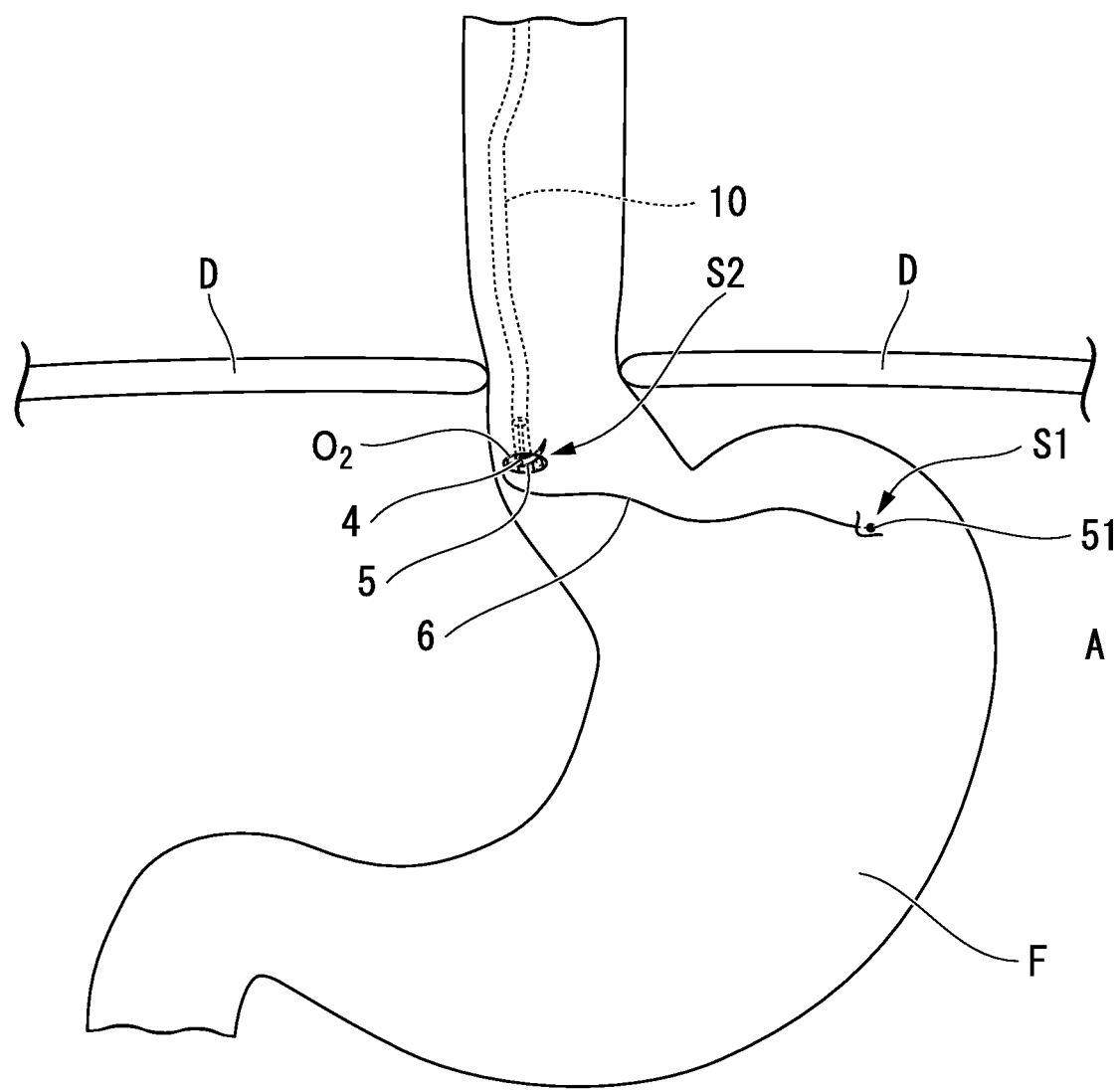
FIG. 8 is a diagram for describing a stenosis forming step in the method for treating reflux esophagitis.

A second end of the suture thread 6 is attached to the suturing needle 5 and a first end thereof includes a first ball stop 51. For this reason, when the operator pulls the suture thread 6 in a direction in which the suturing needle 5 is attached, as illustrated in FIG. 8, the first ball stop 51 is caught in a first suture region S1 and thus the suture thread 6 is not pulled out of the first suture region S1. Note that a shape of the first end of the suture thread 6 is not limited to a ball stop which is formed in advance. When the shape of the first end of the suture thread 6 is set to a loop shape, the suturing needle 5 pierces the first suture region S1, and then the suturing needle 5 passed through a loop of the first end of the suture thread 6, and the suture thread 6 is not pulled out of the first suture region S1.

Subsequently, as illustrated in FIG. 8, the operator inserts the distal end of the suturing needle 5 into tissues from an inside toward an outside of the canal wall on at least a part of the outer circumference of the digestive canal (stomach G and esophagus E) near the diaphragm D closer to the anus than the diaphragm D (hereinafter referred to as a "second suture region (second treatment region) S2"), causes the distal end of the suturing needle 5 to pierce until the distal end of the suturing needle 5 is appeared from the outer surface of the canal wall (stomach wall) again, and then pulls out the appeared distal end using the needle holder 4. Note that the operator may insert the distal end of the suturing needle 5 into tissues from the outside toward the inside of the canal wall.

Figure 9:
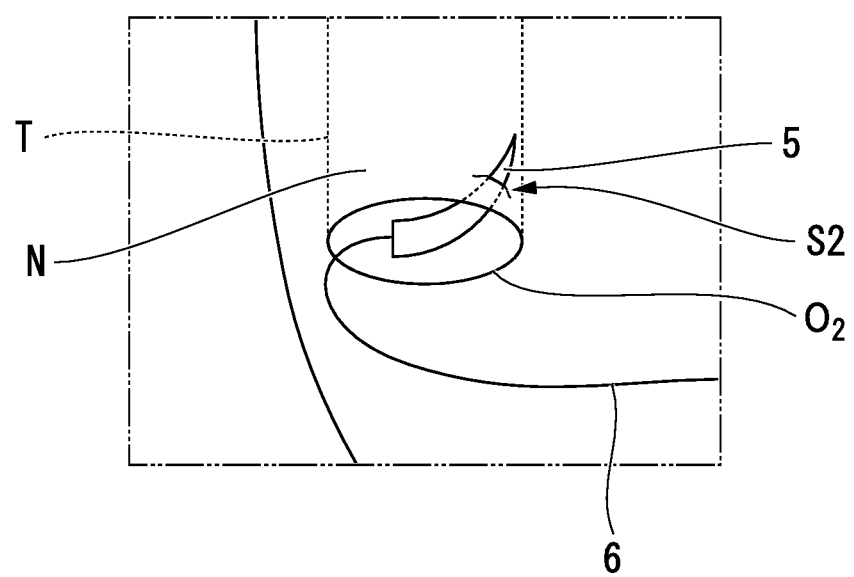
FIG. 9 is a diagram for describing a stenosis forming step in the method for treating reflux esophagitis.

To be specific, as illustrated in FIG. 8, the second suture region S2 is formed in the gastroesophageal junction J or a portion near the gastroesophageal junction J closer to the anus than the diaphragm D. As illustrated in FIG. 9, when the second suture region S2 is located at a periphery of the abdominal cavity side opening $O_2$, the operator can particularly easily perform a procedure of causing the suturing needle 5 to pierce the second suture region S2.

Figure 10:
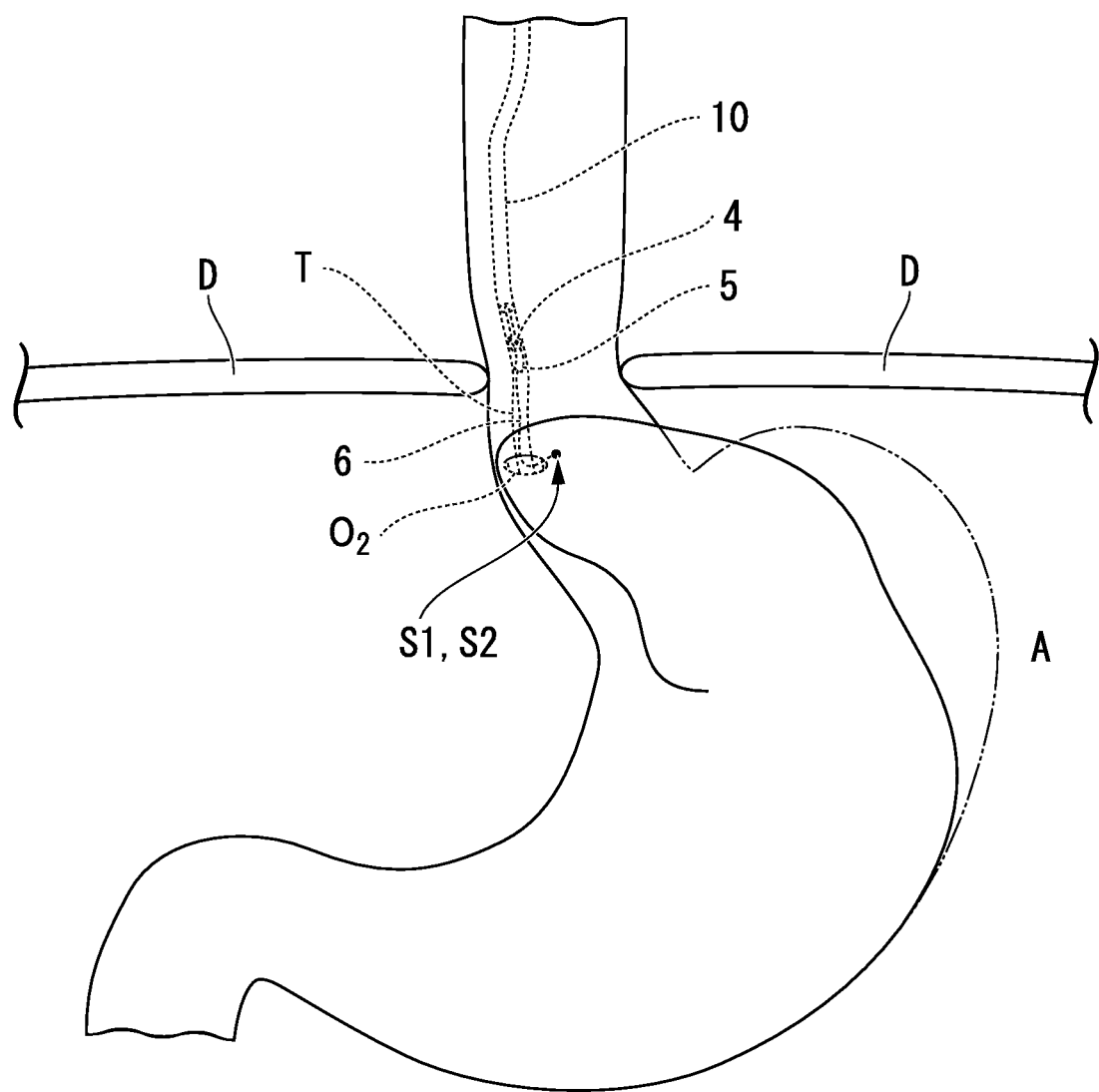
FIG. 10 is a diagram for describing a stenosis forming step in the method for treating reflux esophagitis.

As illustrated in FIG. 10, when the operator moves the insertion part 10 of the endoscope 1 rearward while holding the suturing needle 5 with the needle holder 4, the suturing needle 5 is drawn from the abdominal cavity side opening $O_2$ into the tunnel T. The operator moves the insertion part 10 of the endoscope 1 rearward until the first suture region S1 is gathered close to the second suture region S2.

The operator fixes the first suture region S1 to the second suture region S2 in a state in which the first suture region S1 is gathered close to the second suture region S2. Here, in the state in which the first suture region S1 is gathered close to the second suture region S2, a part of the front wall F of the stomach G having the first suture region S1 formed therein is gathered close to the gastroesophageal junction J having the second suture region S2 formed therein or a portion near the gastroesophageal junction J.

To be specific, as illustrated in FIG. 9, the first suture region S1 is gathered close to the muscle layer N of a periphery of the abdominal cavity side opening $O_2$ at which the second suture region S2 is located, the muscle layer N being located between the tunnel T and the abdominal cavity A.

Figure 11:
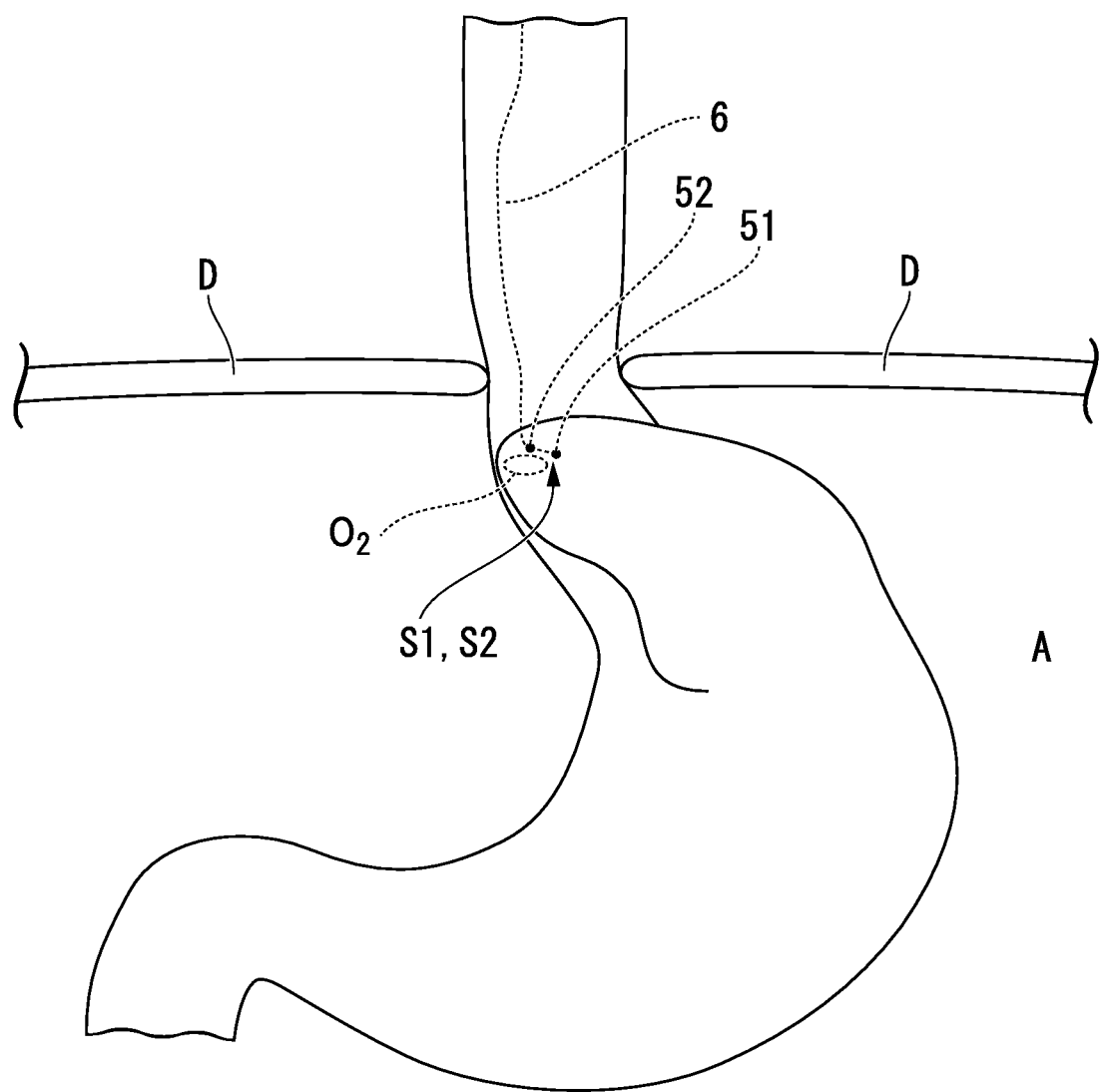
FIG. 11 is a diagram for describing a stenosis forming step in the method for treating reflux esophagitis.

The operator removes the insertion part 10 from the tunnel T and the esophagus E and takes the suturing needle 5 out of the body. The operator removes the suture thread 6 from the suturing needle 5 that has been taken out and forms a knot in the suture thread 6. Subsequently, the operator moves the knot to the second suture region S2. As illustrated in FIG. 11, the operator tightly tightens the knot in contact with the second suture region S2 to form a second ball stop 52. The first suture region S1 and the second suture region S2 are fixed by the first ball stop 51 and the second ball stop 52 so that their relative distance is not changed.

Note that, if the suture thread 6 has a plurality of barbs and is a suture thread in which the suturing needle 5 is allowed to move only in a direction in which it is attached, the second ball stop 52 is not necessarily required.

A part of the front wall F of the stomach G is gathered close to at least a part of the outer circumference of the digestive canal near the diaphragm D closer to the anus than the diaphragm D and fixed and thus a wrap is formed on at least a part of the outer circumference of the digestive canal near the diaphragm D closer to the anus than the diaphragm D and a local stenosis is formed inside the digestive canal in which the wrap is formed.

Figure 12:
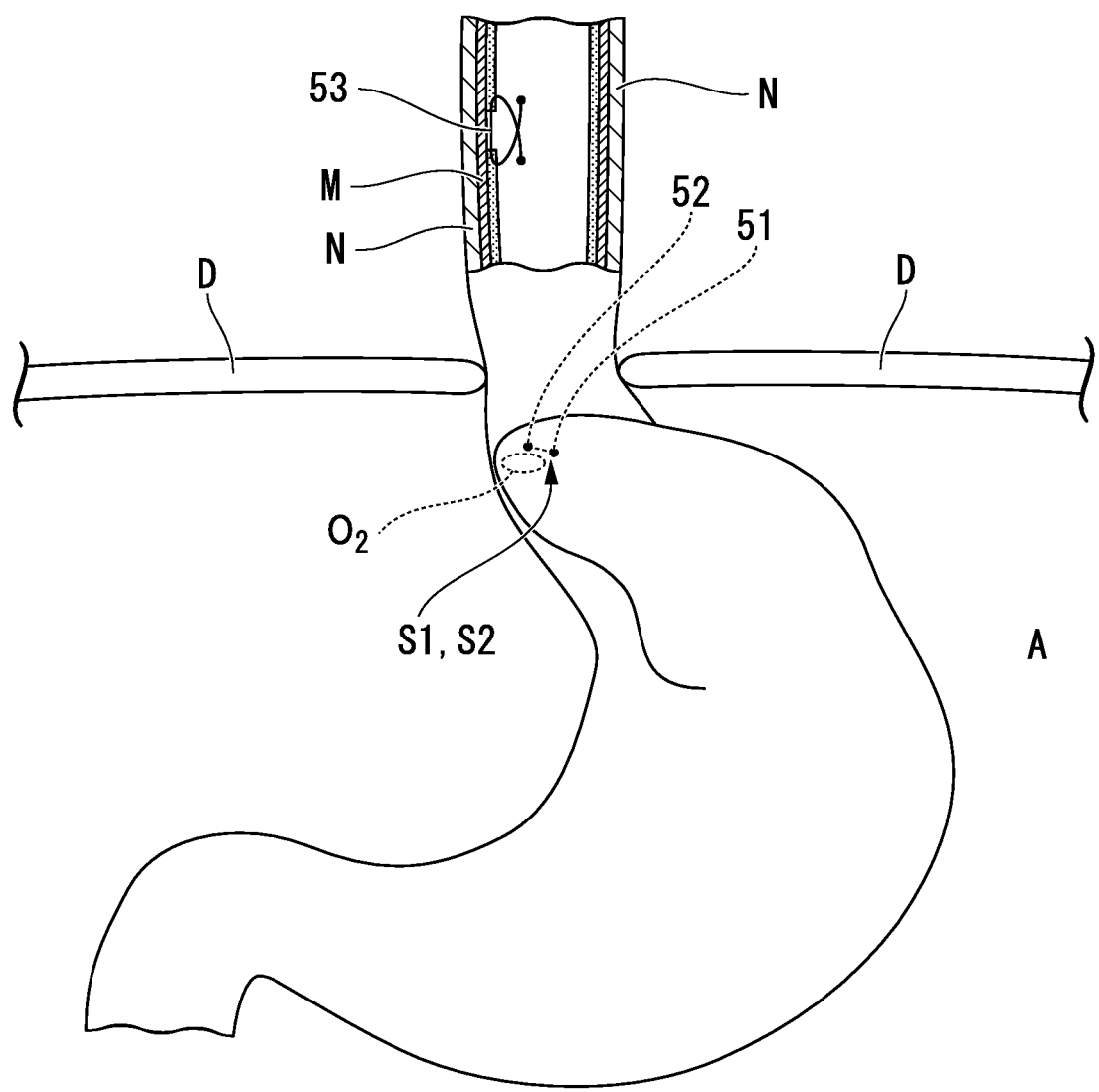
FIG. 12 is a diagram for describing a stenosis forming step in the method for treating reflux esophagitis.

Finally, as illustrated in FIG. 12, the operator sutures the esophageal side opening $O_1$ with a knot 53 to be formed using another suturing needle 5 and suture thread 6 and finishes the procedure.

Note that, if the suture thread 6 has a plurality of bards and is a suture thread in which the suturing needle 5 is allowed to move only in a direction in which it is attached, the knot 53 is not necessarily required.

According to the method for treating reflux esophagitis in the embodiment, invasiveness is minimal without requiring cutting of the abdominal wall, a wrap which can suitably prevent reflux can be formed on at least a part of the outer circumference of the digestive canal, and a local stenosis can be formed inside the digestive canal in which the wrap is formed.

The tunnel T is formed between the mucosal layer M and the muscle layer N at a part of the esophagus and a medical instrument such as the needle holder 4 is delivered into the abdominal cavity A via the tunnel T. Thus, a patient's physical burden is less than that of laparoscopic surgery.

Although the first embodiment of the present invention has been described in detail above with reference to the drawings, a specific constitution is not limited to the embodiment, and design changes are possible without departing from the gist of the present invention. Furthermore, constituent elements illustrated in the above first embodiment and the following modifications can be constructed by appropriately combining them.

(Modification 1)

For example, although the second suture region S2 is disposed at the periphery of the abdominal cavity side opening $O_2$ in the above embodiment, a positional relationship between the abdominal cavity side opening $O_2$ and the second suture region S2 is not limited thereto. The abdominal cavity side opening $O_2$ may be disposed at a position away from the second suture region S2. When the insertion part 10 of the endoscope 1 inserted from the abdominal cavity side opening $O_2$ into the abdominal cavity A is moved, the second suture region S2 at the position away from the abdominal cavity side opening $O_2$ can be treated.

(Modification 2)

For example, although both of the first suture region S1 and the second suture region S2 are formed by one stitch in the above embodiment, an aspect of the first suture region S1 and the second suture region S2 is not limited thereto. The first suture region S1 and the second suture region S2 may be formed by two or more stitches. The first suture region S1 and the second suture region S2 can be more firmly fixed.

(Modification 3)

For example, although the first suture region S1 and the second suture region S2 are sutured in the above embodiment, an aspect of a suture is not limited thereto. For example, when the operator sutures the first suture region S1 and the second suture region S2 and then gathers a third suture region in the canal wall in the vicinity of the first suture region S close to a fourth suture region in the canal wall in the vicinity of the second suture region S2 and fixes (sutures) them, fixation between the first suture region S1 and the second suture region S2 can be reinforced. Note that the fixation between the first suture region S1 and the second suture region S2 can be further reinforced by repeating this if necessary.

(Modification 4)

For example, although the first suture region S1 is formed in a part of the front wall F of the stomach G away from the abdominal cavity side opening $O_2$ in the above embodiment, a forming position of the first suture region S1 is not limited thereto. The first suture region S1 may be a part of the fundus of the stomach, which is a site that can be easily treated. When the first suture region S1 is gathered close to the second suture region S2 and fixed regardless of what portion of the stomach G the first suture region S1 is formed in and a wrap is formed in the second suture region S2, a local stenosis can be formed inside the digestive canal in which the wrap is formed.

A second embodiment of the present invention will be described with reference to FIGS. 13 to 16. In the following description, constituent elements that are the same as those which have already been described will be denoted with the same reference numerals and overlapping description thereof will be omitted. A method for treating reflux esophagitis according to the second embodiment and the method for treating reflux esophagitis according to the first embodiment differ in that the method for treating reflux esophagitis according to the second embodiment does not use a suture thread in a stenosis forming step but uses a clip and a detachable snare.

The method for treating reflux esophagitis according to the second embodiment includes an insertion step to a protrusion step that are the same as the insertion step to the protrusion step in the method for treating reflux esophagitis according to the first embodiment.

[Stenosis Forming Step]

FIGS. 13 to 16 are diagram for describing a stenosis forming step in the method for treating reflux esophagitis according to the embodiment. When the operator forms a wrap on at least a part of an outer circumference of a digestive canal (stomach G and esophagus E) near a diaphragm D closer to an anus than the diaphragm D using a medical instrument inserted into a treatment instrument insertion channel 12 of an endoscope 1 in an abdominal cavity A, a local stenosis is formed inside the digestive canal having the wrap formed therein (stenosis forming step).

Figure 13:
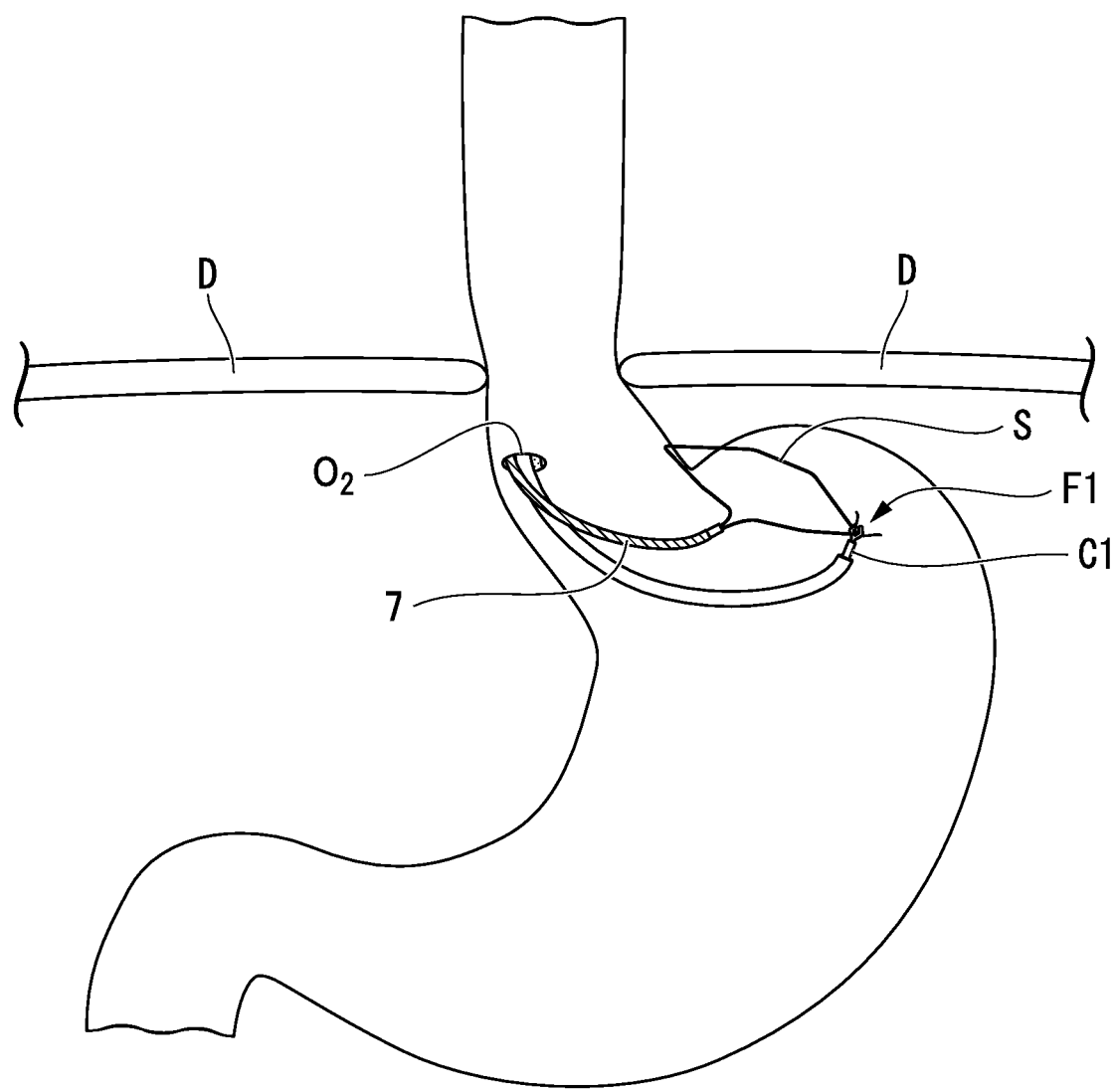
FIG. 13 is a diagram for describing a stenosis forming step in a method for treating reflux esophagitis according to a second embodiment of the present invention.

As illustrated in FIG. 13, the operator delivers a clip C1 sandwiching a detachable snare S attached to an applicator 7 from a distal end opening portion 12a of an insertion part 10 of the endoscope 1 protruding from an abdominal cavity side opening $O_2$ to the abdominal cavity A into the abdominal cavity A. As illustrated in FIG. 13, the operator attaches the clip C1 to a part of a front wall F of the stomach G away from the abdominal cavity side opening $O_2$. In the following description, a portion to which the clip C1 is attached will be referred to as a "first attachment region (first treatment region) F1."

Figure 14:
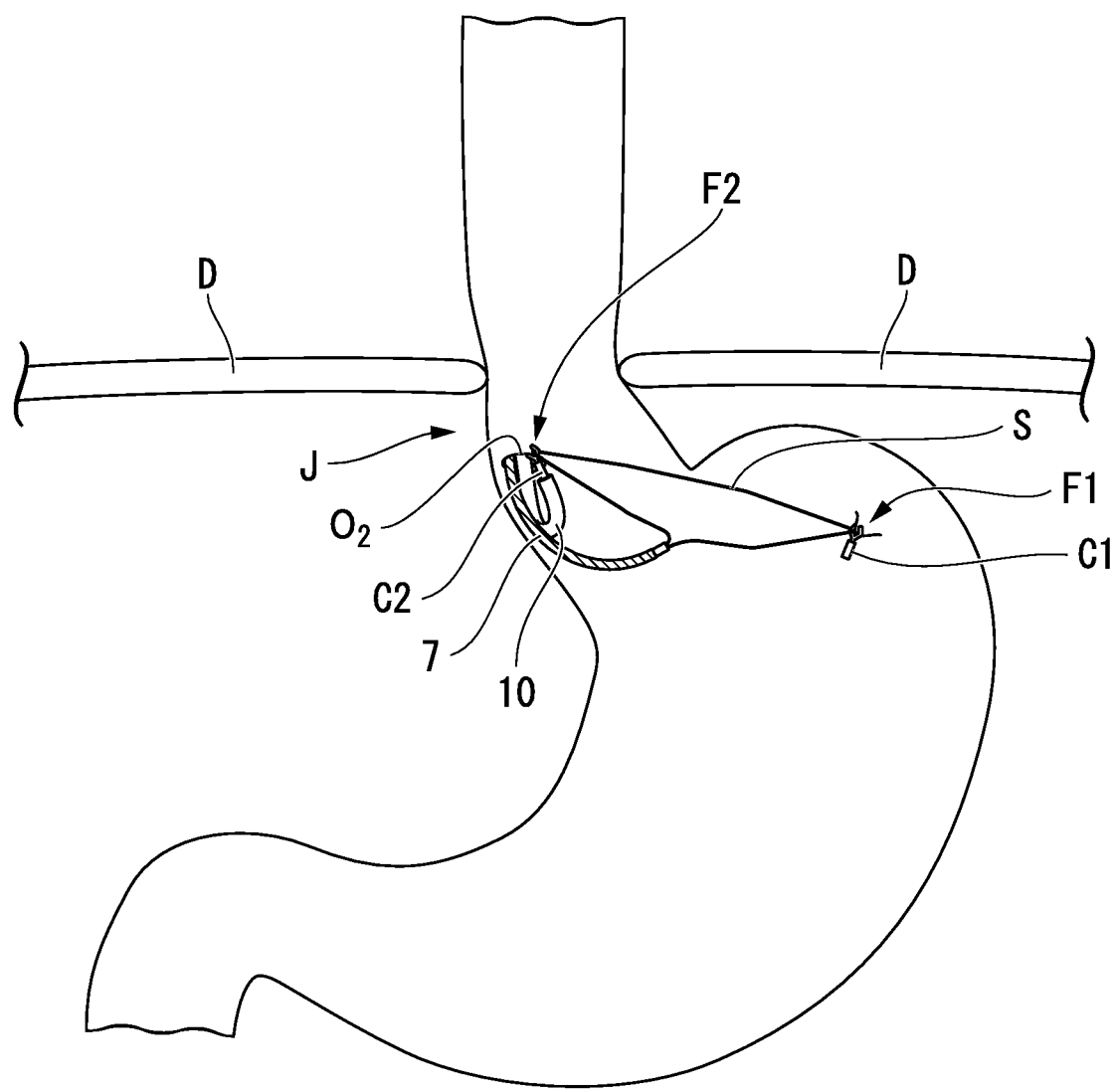
FIG. 14 is a diagram for describing a stenosis forming step in the method for treating reflux esophagitis.

Subsequently, the operator delivers a clip C2 into the abdominal cavity A. As illustrated in FIG. 14, the operator sandwiches the detachable snare S with the clip C2 and attaches the clip C2 sandwiching the detachable snare S to a canal wall on at least a part of the outer circumference of the digestive canal (stomach G and esophagus E) near the diaphragm D closer to the anus than the diaphragm D. At this time, in the abdominal cavity A, a distal end portion of the endoscope 1 is bent. In the following description, a portion to which the clip C2 is attached will be referred to as a "second attachment region (second treatment region) F2." As illustrated in FIG. 14, the second attachment region F2 is preferably at a periphery of the abdominal cavity side opening $O_2$, more preferably in a muscle layer N of the periphery of the abdominal cavity side opening $O_2$, the muscle layer N being located between a tunnel T and an abdominal cavity A.

Figure 15:
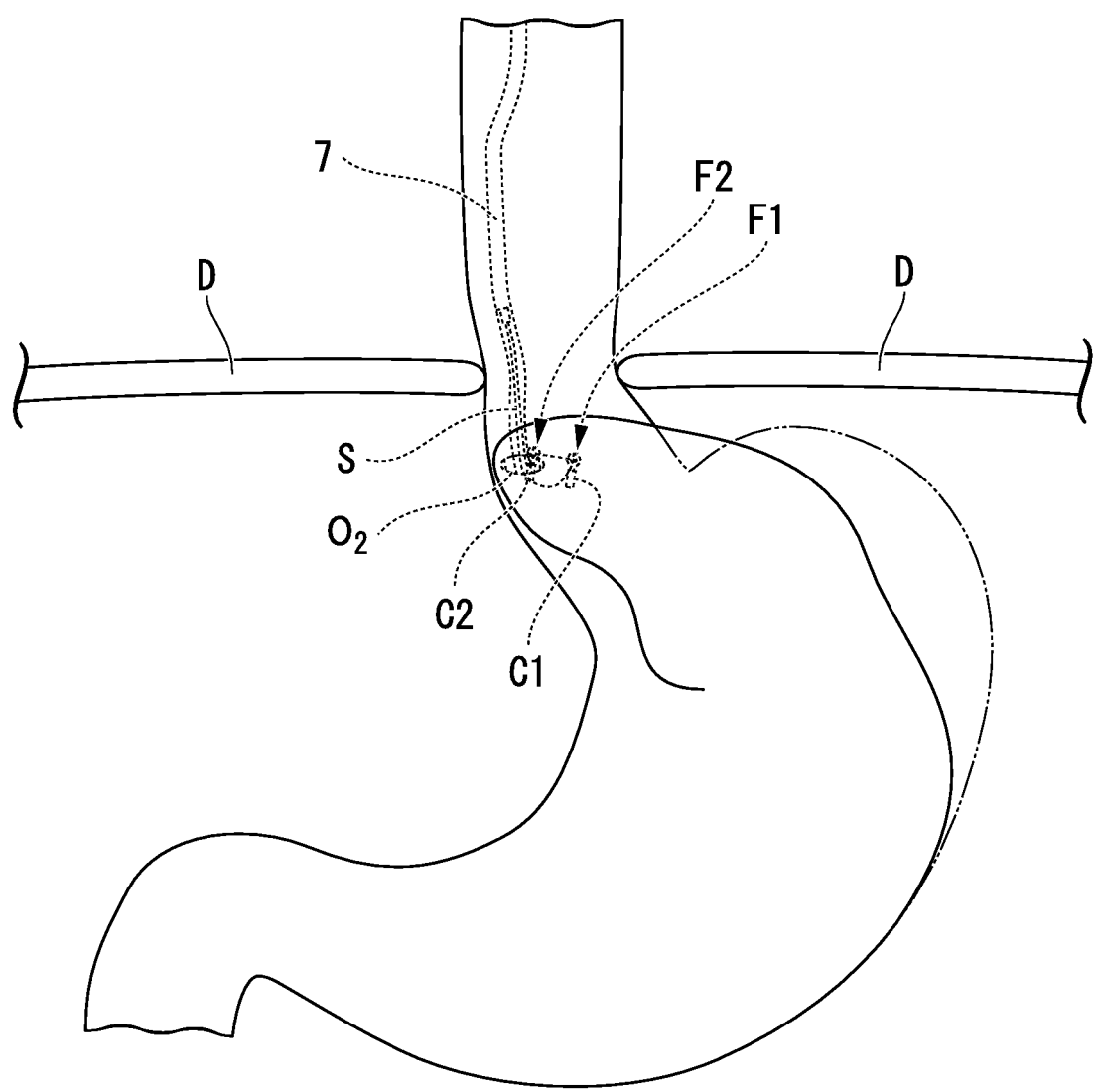
FIG. 15 is a diagram for describing a stenosis forming step in the method for treating reflux esophagitis.
Figure 16:
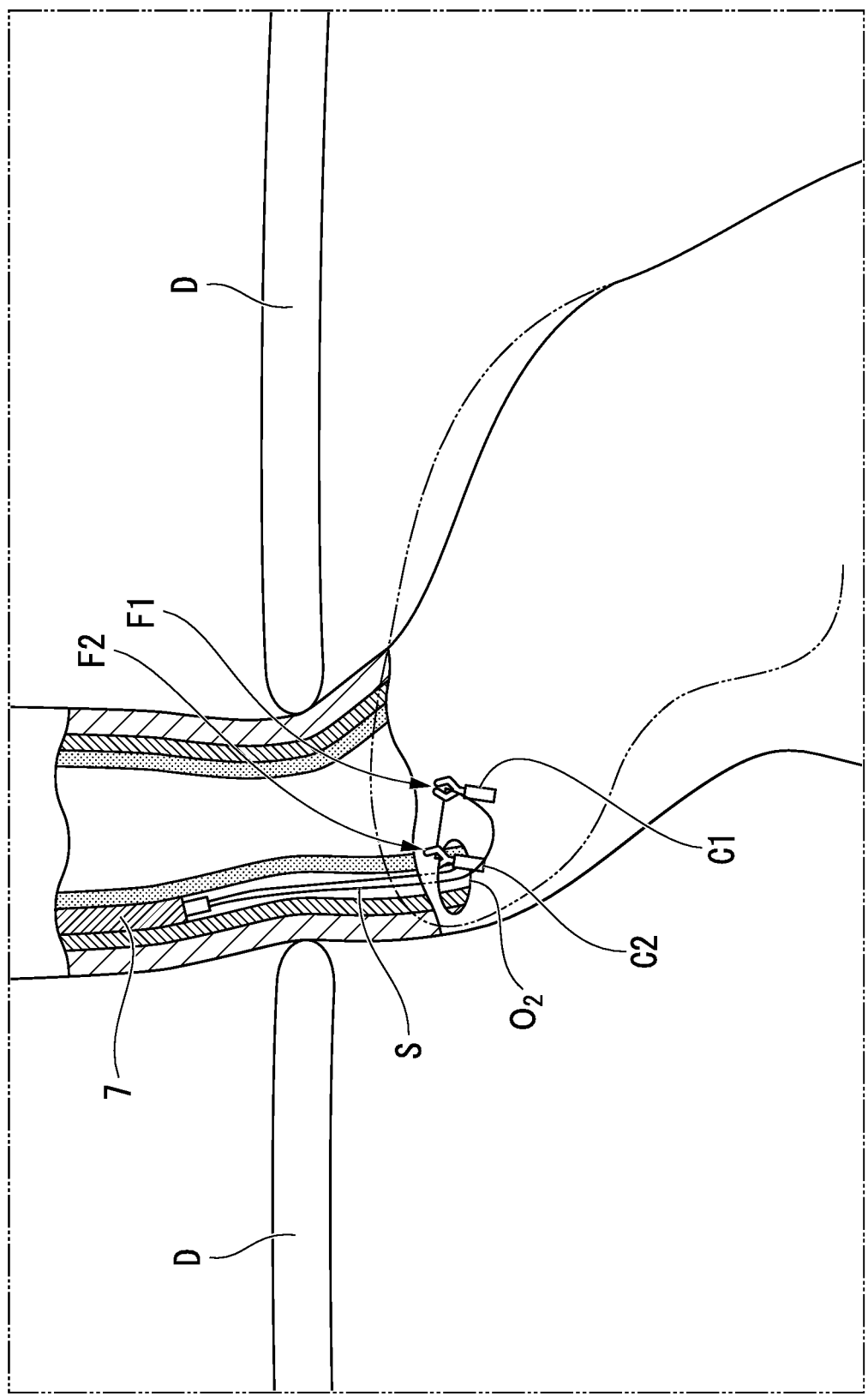
FIG. 16 is an enlarged cross-sectional view of FIG. 15.

As illustrated in FIG. 15 and FIG. 16 that is an enlarged cross-sectional view of FIG. 15, the operator moves the insertion part 10 of the endoscope 1 rearward while attaching the applicator 7 to the detachable snare S to draw an end portion of the detachable snare S from the abdominal cavity side opening $O_2$ to the tunnel T. The operator narrows an aperture of the detachable snare S with the applicator 7 until the first attachment region F1 is gathered close to the second attachment region F2. The aperture of the detachable snare S is narrowed and thus the first attachment region F1 and the second attachment region F2 are fixed so that their relative distance is not changed.

A part of the front wall F of the stomach G is gathered close to at least a part of the outer circumference of the digestive canal near the diaphragm D closer to the anus than the diaphragm D and fixed and thus a wrap is formed on at least a part of the outer circumference of the digestive canal near the diaphragm D closer to the anus than the diaphragm D and a local stenosis is formed inside the digestive canal in which the wrap is formed.

Finally, the operator closes an esophageal side opening $O_1$ using a clip and finishes the procedure. Note that, like in the first embodiment, the operator may suture the esophageal side opening $O_1$ with a knot 53 to be formed using another suturing needle 5 and suture thread 6 and finishes the procedure.

According to the method for treating reflux esophagitis in the embodiment, invasiveness is minimal without requiring cutting of the abdominal wall, a wrap which can suitably prevent reflux can be formed on at least a part of the outer circumference of the digestive canal, and a local stenosis can be formed inside the digestive canal in which the wrap is formed.

The tunnel T is formed between the mucosal layer M and the muscle layer N at a part of the esophagus and a grasping forceps or the like is delivered into the abdominal cavity A via the tunnel T. Thus, a physical burden on a patient is less than that of laparoscopic surgery.

Although the second embodiment of the present invention has been described in detail above with reference to the drawings, a specific constitution thereof is not limited to the embodiment, and design changes are possible without departing from the gist of the present invention. Furthermore, constituent elements illustrated in the above second embodiment and the modifications of the first embodiment can be constructed by appropriately combining them.

The invention claimed is:

1. A method for treating reflux esophagitis comprising:
orally inserting an endoscope into a digestive canal;
forming an esophageal side opening in a mucosal layer in a part of an esophagus;
introducing the endoscope between the mucosal layer and a muscle layer from the esophageal side opening and forming a tunnel;
forming an abdominal cavity side opening passing from the tunnel to an abdominal cavity at a position on the digestive canal that is between an anus and a diaphragm;
protruding a distal end portion of the endoscope passing through the tunnel from the abdominal cavity side opening into the abdominal cavity; and
forming a wrap on at least a part of an outer circumference of the digestive canal at a position that is: (i) between the diaphragm and the anus, and (ii) closer to the diaphragm than the position is to the anus, using a medical instrument inserted into a channel of the endoscope in the abdominal cavity to form a local stenosis inside the digestive canal on which the wrap is formed.

2. The method for treating reflux esophagitis according to claim 1, wherein:
the abdominal cavity side opening opens on a side of the digestive canal on which a front wall of a stomach is disposed, and
the wrap is formed in a state in which a part of the front wall that is away from the abdominal cavity side opening is gathered towards a portion of the digestive canal that is: (i) near the diaphragm, and (ii) between the anus and the diaphragm, such that the part of the front wall is fixed to the portion of the digestive canal by the wrap.

3. The method for treating reflux esophagitis according to claim 2, wherein the formation of the wrap includes:
gathering the part of the front wall towards the portion of the digestive canal; and
fixing the part of the front wall to the portion of the digestive canal in a state in which the part of the front wall is gathered towards the portion of the digestive canal.

4. The method for treating reflux esophagitis according to claim 2, wherein:
the abdominal cavity side opening is formed in a gastroesophageal junction or a region of the digestive canal that is (i) near the gastroesophageal junction, and (ii) between the anus and the diaphragm, and
the wrap is formed in a state in which the part of the front wall of the stomach that is away from the abdominal cavity side opening is gathered towards the gastroesophageal junction or the region of the digestive canal, such that the part of the front wall is fixed to the gastroesophageal junction or the region of the digestive canal by the wrap.

5. The method for treating reflux esophagitis according to claim 4, wherein the formation of the wrap includes:
gathering the part of the front wall that is away from the abdominal cavity side opening towards the gastroesophageal junction or the region of the digestive canal; and
fixing the part of the front wall to the gastroesophageal junction or the region of the digestive canal in a state in which the part of the front wall is gathered towards the gastroesophageal junction or the region of the digestive canal.

6. The method for treating reflux esophagitis according to claim 2, wherein
the part of the front wall is fixed to the portion of the digestive canal by forming the wrap in a state in which the part of the front wall is gathered towards a portion of the muscle layer that is positioned at a periphery of the abdominal cavity side opening, the portion of the muscle layer being located between the tunnel and the abdominal cavity.

7. The method for treating reflux esophagitis according to claim 2, wherein during the formation of the wrap:
a first end of a suture thread is fixed to the part of the front wall that is away from the abdominal cavity side opening,
the suture thread is caused to pass through a canal wall at a periphery of the abdominal cavity side opening, and the wrap is formed by fixing the part of the front wall to the periphery of the abdominal cavity side opening in a state in which the part of the front wall is gathered towards the periphery of the abdominal cavity side opening by pulling a second end of the suture thread.

* * * * *